United States Patent [19]

Finkelstein et al.

[11] Patent Number: 5,422,247

[45] Date of Patent: * Jun. 6, 1995

[54] BLAKESLEA TRISPORA MATED CULTURE CAPABLE OF INCREASED BETA-CAROTENE PRODUCTION

[75] Inventors: Mark Finkelstein, Ft. Collins, Colo.; Chien-Chang Huang, Taipei, Taiwan, Prov. of China; Graham S. Byng, Woodinville, Wash.; Bi-Ru Tsau, Taipei Hsien, Taiwan, Prov. of China; Jeanette Leach, Boulder, Colo.

[73] Assignee: Universal Foods Corporation, Milwaukee, Wis.

[*] Notice: The portion of the term of this patent subsequent to Jul. 12, 2011 has been disclaimed.

[21] Appl. No.: 155,438

[22] Filed: Nov. 19, 1993

Related U.S. Application Data

[63] Continuation of Ser. No. 858,145, Mar. 27, 1992, abandoned.

[51] Int. Cl.$^6$ .......................... C12P 23/00; C12P 1/02; C12N 1/14
[52] U.S. Cl. .................. 435/67; 435/254.1; 435/171; 435/911
[58] Field of Search ............. 435/254.1, 67, 171, 435/911

[56] References Cited

U.S. PATENT DOCUMENTS

| | | | |
|---|---|---|---|
| 2,865,814 | 12/1958 | Hesseltine et al. | 435/42 |
| 2,890,989 | 6/1959 | Anderson | 435/67 |
| 2,910,410 | 10/1959 | Corman | 435/67 |
| 2,959,521 | 11/1960 | Zajic | 435/67 |
| 2,959,522 | 11/1960 | Zajic | 435/67 |
| 3,001,912 | 9/1961 | Miescher | 435/67 |
| 3,095,357 | 6/1963 | Fulde | 435/67 |
| 3,128,236 | 4/1964 | Zajic | 195/28 |
| 3,226,302 | 12/1965 | Ciegler | 435/67 |
| 3,235,467 | 2/1966 | Ninet et al. | 435/67 |
| 3,242,054 | 3/1966 | Ninet et al. | 435/67 |
| 3,291,701 | 12/1966 | Fulde | 435/67 |
| 3,378,460 | 4/1968 | Ninet et al. | 435/67 |
| 3,421,980 | 1/1969 | Ninet et al. | 435/67 |
| 3,492,202 | 1/1970 | Bohinski | 435/67 |
| 3,522,146 | 7/1970 | Jager | 435/167 |
| 4,318,987 | 3/1982 | Araujo et al. | 435/172 |
| 5,328,845 | 7/1994 | Finkelstein et al. | 435/254.1 |

OTHER PUBLICATIONS

Murillo et al., "Carotene–Superproducing Strains of *Phycomyces*", *Applied and Environmental Microbiology*, vol. 36, No. 5, pp. 639–642, 1978.

Salgado et al., "Carotene–Superproducing Mutants of *Phycomyces blakesleeanos*", *Experimental Mycology*, vol. 13, pp. 332–336, 1989.

Cruerger et al., "Strain Development", In: Biotechnology: A Textbook of Industrial Microbiology, Pubumis:-Sinauer Associates Inc., pp. 9–17, 1984.

(List continued on next page.)

*Primary Examiner*—Marion C. Knode
*Assistant Examiner*—Susan M. Dadio
*Attorney, Agent, or Firm*—Whyte Hirschboeck Dudek

[57] ABSTRACT

The present invention is directed toward a method for producing beta-carotene using a mated culture of Mucorales fungi. The method includes mutating and selecting negative (minus mating type) and positive (plus mating type) Mucorales fungal microorganisms, culturing the selected negative and positive microorganisms in an effective medium to form a mated culture that produces beta-carotene, and recovering beta-carotene therefrom. The present invention provides mated cultures that overproduce beta-carotene and is also directed to certain negative and positive microorganisms used to overproduce beta-carotene. The present invention also provides beta-carotene formulations produced by the claimed method, and the use of such formulations, for example, to enhance pigmentation, to reduce damage caused by reactive oxygen species or phototoxic molecules, to prevent or treat cancer or cardiovascular disease, to provide a Vitamin A supplement, to enhance lactation, and to increase fertility.

25 Claims, No Drawings

OTHER PUBLICATIONS

Jacobson, G. K. "Mutations", In: Biotechnology, vol. 1, Rehm et al. (eds), Publisher: Verlag Chemie, pp. 297–299, 1981.

L. Ninet, J. Renaut and R. Tissier, *Activation of the Biosynthesis of Carotenoids by Blakeslea trispora*, Biotechnology and Bioengineering, vol. XI, pp. 1195–1210 (1969).

L. Ninet and J. Renaut, *Carotenoids*, Microbial Technology, 2nd ed., vol. 1, pp. 529–544 (1979).

H. J. Nelis and A. P. De Leenheer, *A Review: Microbial Sources of Carotenoid Pigments Used in Foods and Feeds*, Journal of Applied Bacteriology, vol. 70, pp. 182–184 (1991).

Hanson, A., *Production of Pigments and Vitamins*, Microbial Technology, pp. 222–250 (1977).

Ciegler, et al., *Effect of Various Grains on Production of Beta-Carotene by Mated Strains of Blakeslea trispora*, Microbial Production of Carotenoids IV, pp. 94–97 (1958).

Nelis et al., "Microbial Sources of Carotenoid Pigments Used in Foods and Feeds", pp. 181–191, 1991, Journal of Applied Bacteriology, vol. 70.

Murillo et al., "Carotene-Superproducing Strains of Phycomyces", pp. 639–642, 1978, Appl. Environ. Microbiol., vol. 36.

Lampila et al., "A Review of Factors Affecting Biosynthesis of Carotenoids by the Order Mucorales", pp. 65–80, 1985, Mycopathologia, vol. 90.

Cerda-Olmedo, "Production of Carotenoids with Fungi", pp. 27–42, 1989, Biotechnology of Vitamins, Pigments, and Growth Factors, (E. Vandamme, ed).

BLAKESLEA TRISPORA MATED CULTURE CAPABLE OF INCREASED BETA-CAROTENE PRODUCTION

This is a continuation of application Ser. No. 07/858,145 filed on Mar. 27, 1992, now abandoned.

FIELD OF THE INVENTION

The present invention relates generally to a method for producing beta-carotene and to certain fungal microorganisms capable of producing improved yields of beta-carotene. More particularly, the invention relates to the production of beta-carotene by fermenting novel minus mating type (negative) *Blakeslea trispora* microorganisms and novel plus mating type (positive) *Blakeslea trispora* microorganisms together as mated cultures.

BACKGROUND OF THE INVENTION

The carotenoid beta-carotene is a pigment useful in enhancing the pigmentation of animal foodstuffs, food products and cosmetics. Typically, beta-carotene provides yellow to yellow-orange pigmentation. Beta-carotene also serves as a precursor of Vitamin A (retinol) in both animals and man. In addition, beta-carotene, like some other carotenoids, is an effective antioxidant. Epidemiological studies suggest the use of beta-carotene to prevent or treat certain types of cancer and to reduce cellular or tissue damage caused by reactive oxygen species and phototoxic molecules, such occurs, for example, in cardiovascular disease. Beta-carotene may also be used to stabilize compounds subject to oxidation, particularly when exposed to light.

Due to Food and Drug Administration regulations covering chemically-synthesized products, it is preferable to use biological sources to produce beta-carotene. The carotenoid is known to be synthesized by most green plants as well as by certain algae (e.g., Dunaliella), fungi (e.g., Ascomycetes and Deuteromycetes), cyanobacteria and photosynthetic bacteria. Naturally-occurring Zygomycetes of the order Mucorales, family Choanephoraceae, which includes the genera Blakeslea, Choanephora, Mucor, Parasitella, Phycomyces, and Pilaria are particularly well known producers of beta-carotene. Accumulation of beta-carotene in these fungi is strongly linked to sexual interaction between plus mating type (positive) and minus mating type (negative) microorganisms of such fungi. For example, mating of positive and negative wild-type (i.e., naturally-occurring) Blakeslea is known to result in a 5-fold to 20-fold increase in beta-carotene production compared to single, non-mated wild-type microorganisms.

Several companies in the 1960's used naturally-occurring negative and positive *Blakeslea trispora* microorganisms that, when mixed together (i.e., mated), were reported to produce up to 3 to 3.5 grams of beta-carotene per liter of medium in 10-day to 12-day fermentations. See, for example, Nelis et al., 1991, *J. Appl. Bacteriol.* 70, 181–191. Investigators have shown that beta-factor, a hormone-like substance that is produced upon mating, stimulates beta-carotene production in Blakeslea. The major component of beta-factor is trisporic acid. Other chemicals that stimulate beta-carotene production include beta-ionone, retinol, kerosene, aromatics (such as dimethyl phthalate and veratrol), and nitrogenous heterocyclic compounds (such as isoniazid and iproniazid). However, past efforts to produce beta-carotene have focussed primarily on improving fermentation conditions rather than on the use of genetic selection techniques to improve beta-carotene production.

SUMMARY OF THE INVENTION

The present invention is directed toward a method for producing beta-carotene using a mated culture of Mucorales fungi. The method includes (a) mutating negative and positive Mucorales fungal microorganisms; (b) selecting from the mutated microorganisms negative and positive microorganisms which, when mixed together form a mated culture that is capable of producing at least about 2.7 grams of beta-carotene per liter of medium in about 7 days; (c) culturing selected negative and positive microorganisms in an effective medium to produce beta-carotene; and (d) recovering beta-carotene therefrom.

The present invention provides mated cultures that overproduce beta-carotene and is also directed to certain negative and positive microorganisms used to overproduce beta-carotene. Preferred methods for selecting negative and positive microorganisms include selecting microorganisms exhibiting a pigmentation indicative of beta-carotene production and/or selecting microorganisms having the capability of growing in the presence of an effective selective agent. Mated cultures of the present invention preferably are able to produce at least about 3.5 grams of beta-carotene per liter of medium in about 7 days, more preferably are able to produce at least about 4 grams of beta-carotene per liter of medium in about 7 days, even more preferably are able to produce at least about 6 grams of beta-carotene per liter of medium in about 7 days, and even more preferably are able to produce at least about 7 grams of beta-carotene per liter of medium in about 7 days. Preferred negative microorganisms of the present invention are of the genus Blakeslea, including *B. trispora* ATCC No. 74146 (PF17-12), *B. trispora* ATCC No. 74147 (PF17-13), and mutants thereof. Preferred positive microorganisms of the present invention are of the genus Blakeslea, including *B. trispora* ATCC No. 74145 (PF17-10) and mutants thereof.

The invention also discloses a preferred mating ratio of at least about 4 negative microorganisms per positive microorganism to produce a mated culture. More preferred mating ratios of at least about 10, and even more preferably at least about 40, negative microorganisms per positive microorganism are disclosed. In a more preferred embodiment, the mating ratio is from about 40 to about 200 negative microorganisms per positive microorganism.

The present invention is also directed toward a beta-carotene-containing biomass and beta-carotene-containing formulations produced by the claimed method. Beta-carotene produced according to the present invention can be used, among other things, to enhance the pigmentation of animal foodstuffs, other food products, and cosmetics; to reduce damage caused by reactive oxygen species or phototoxic molecules; to prevent or treat cancer or cardiovascular disease; to provide a Vitamin A supplement; to enhance lactation; and to increase fertility.

DETAILED DESCRIPTION OF THE INVENTION

Mucorales fungal microorganisms exhibit both asexual and sexual modes of reproduction. Mucorales fungi generally exist as non-mated microorganisms of opposite mating types. As used herein, a "non-mated microorganism" is a microorganism that is either of a negative (minus) or a positive (plus) mating type depending on its sexual characteristics. As used herein, a "microorganism of one mating type" can refer to either a negative microorganism or to a positive microorganism, depending on the microorganism's sexual characteristics. If a microorganism of one mating type is positive, then a "microorganism of the opposite mating type" is negative, and vice versa.

Both negative and positive microorganisms can be either spores or mycelia depending on their stage in a fungal life cycle. For example, during the asexual mode of replication, a non-mated microorganism spore germinates into a mycelium. When the mycelium has grown to an appropriate size, it produces aerial hyphae containing sporangia filled with spores. During the sexual mode of reproduction, a negative microorganism interacts with a positive microorganism to form a mated culture.

Without being bound by theory, it is believed that this sexual interaction triggers signals by negative and/or positive microorganisms that stimulate beta-carotene production by the mated culture. While negative microorganisms typically produce significantly more beta-carotene than do positive microorganisms, the highest levels of beta-carotene production generally occur when negative and positive microorganisms are physically contacting each other. For example, it is known that wild-type mated cultures of negative and positive Mucorales fungal microorganisms are capable of producing at least about 5-times to 20-times as much beta-carotene as are wild-type non-mated microorganisms. However, mated cultures are not stable, and, thus, each fermentation to produce beta-carotene requires the culturing of positive and negative microorganisms in separate fermentations until each grows to an effective cell density, followed by the mixing together (or mating) of the negative and positive microorganisms to form a mated culture capable of producing additional beta-carotene.

In accordance with the present invention, negative and/or positive microorganisms are targeted for genetic strain improvement. Genetically-improved microorganisms of opposite mating types can then be mixed together to form a mated culture which can be analyzed for beta-carotene production. A preferred technique to genetically improve negative and positive microorganisms so as to overproduce beta-carotene is the use of mutation and selection strategies, as described below.

In one aspect of the present invention, the use of mutation and selection strategies to genetically improve a negative Mucorales fungal microorganism results in the production of a negative Mucorales fungal microorganism, which when mated to a positive fungal microorganism, forms a mated culture capable of overproducing beta-carotene. Similarly, the use of the present mutation and selection strategies to genetically improve a positive Mucorales fungal microorganism results in the production of a positive fungal microorganism, which when mated to a negative fungal microorganism, forms a mated culture capable of overproducing beta-carotene. As used herein, "mating" refers to the mixing together of negative and positive microorganisms in an environment which allows them to interact sexually to form a mated culture. Preferably the negative and positive microorganisms physically interact, triggering high levels of beta-carotene production. A "mated culture capable of overproducing beta-carotene" is a mated culture that is capable of producing at least about 2.7 grams of beta-carotene per liter of medium in about 7 days. Preferably, a mated culture capable of overproducing beta-carotene is capable of producing at least about 65 milligrams (mg) of beta-carotene per gram of dry cell weight.

Parental microorganisms refer to any negative or positive Mucorales fungal microorganisms to be mutated, and may include, but are not limited to, naturally-occurring (wild-type), variant, previously mutated, and previously selected microorganisms. In the present invention, preferred parental microorganisms are negative and positive Mucorales fungi of the family Choanephoraceae, particularly of the genus Blakeslea, and more particularly those of the species *Blakeslea trispora*.

As used herein, a "mutated microorganism" is a negative or positive Mucorales fungal microorganism in which a mutation either occurs naturally or results from intentional exposure of the microorganism to a mutagen. In a preferred embodiment of the present invention, a parental microorganism is subjected to at least one round of chemical or physical mutagenesis in order to increase the mutation rate, thereby increasing the probability of obtaining a desired microorganism.

In accordance with the present invention, a negative or positive parental Mucorales fungal microorganism is mutated using any suitable mutagen in order to obtain a mutated microorganism. Suitable mutagens include, but are not limited to, N-methyl-N'-nitro-N-nitrosoguanidine (NTG), ethylmethane sulfonate (EMS), nitrous acid, nucleotide analogs, acridines, ultraviolet light (UV), x-rays, gamma rays, and mixtures thereof.

In a preferred embodiment of the present invention, an effective amount of the mutagen NTG is added to a spore suspension of either a positive or negative parental microorganism of *Blakeslea trispora*. The spores are incubated in a buffer medium, such as Tris(hydroxymethyl)-aminomethane (Tris) at a pH of about 8.0, containing from about 10 micrograms ($\mu$g) to about 500 $\mu$g NTG per milliliter (ml) medium for a period of time from about 10 minutes to about 30 minutes at about room temperature. Preferably, *B. trispora* spores are exposed to about 50 $\mu$g NTG per ml of medium for about 20 minutes at about room temperature. After exposure, mutated spores are plated onto a solidified growth medium at about 26° C. to about 28° C., preferably at about 27° C., for about 5 to about 10 days to obtain separate colonies. As used herein, a solidified growth medium refers to a growth medium to which a solidifying agent such as gelatin, agarose, or agar has been added. A preferred solidified growth medium of the present invention is CM17-1, which is an aqueous medium containing glucose, magnesium sulfate, potassium phosphate, L-asparagine, thiamine, yeast extract, and sodium-deoxycholate, to which agar has been added.

In accordance with the present invention, a desired negative or positive microorganism is selected from among all mutated microorganisms. As used herein, a "selected microorganism" or a "desired mutated microorganism" refers to a mutated negative or positive microorganism which when mated to a microorganism of the opposite mating type, is capable of producing more beta-carotene than a parental microorganism. In one embodiment of the present invention, a negative or positive mutated microorganism is selected which displays a pigmentation (i.e., color) indicative of the ability of the microorganism, when mated to a microorganism of the opposite mating, to form a mated culture capable of overproducing beta-carotene. As used herein, "a pigmentation indicative of the ability to produce beta-carotene" includes the colors pale yellow, yellow, yellow-orange, orange, red-orange and red, depending on the selection regimen. For example, red microorganisms may be selected when a selective agent that inhibits the synthesis of beta-carotene from the red pigment lycopene is used. A preferred pigmentation color range for selection of desired negative or positive mutated microorganisms is from about deep yellow to about yellow-orange.

Alternatively, or in addition, a desired mutated microorganism may be selected by its ability to grow in the presence of an effective amount of a selective agent (i.e., by its ability to be resistant to said selective agent). As used herein, an "effective amount of a selective agent" is an amount that typically inhibits the growth of parental microorganisms to a greater extent than the growth of a desired microorganism. Effective selective agents include, but are not limited to, antihypercholesterolemic agents, antihyperlipoproteinemic agents, antihyperlipidemic agents, inhibitors of acetyl CoA synthesis, inhibitors of carotenoid biosynthesis, inhibitors of isoprenoid biosynthesis (including inhibitors of sterol biosynthesis), free radical generators, and mixtures thereof.

In one embodiment of the present invention, a desired mutated microorganism is selected from among all mutated microorganisms by its ability to grow in a medium containing an antihypercholesterolemic agent, an antihyperlipoproteinemic agent, an antihyperlipidemic agent, or a mixture thereof. Antihypercholesterolemic agents, such as lovastatin, typically reduce sterol (e.g., ergosterol) levels in a microorganism. Antihyperlipoproteinemic agents, such as pravastatin and probucol, typically reduce lipoprotein levels in a microorganism. Likewise, antihyperlipidemic agents, such as simvastatin, typically reduce lipid levels in a microorganism. Without being bound by theory, it is believed that microorganisms capable of growing in the presence of these inhibitors are able to shuttle more carbon through the common branch of the carotenoid and sterol biosynthetic pathways. For example, it is believed that microorganisms which are resistant to lovastatin have a modified hydroxy-methyl-glutaryl-coenzyme A (HMG-CoA) reductase enzyme that is no longer inhibited by sterols.

In one embodiment of the present invention, mutated spores are plated onto lovastatin-containing solidified growth medium, such as lovastatin-containing CM17-1, and grown for about 7 days at about 27° C. Preferred concentrations of lovastatin in the medium are from about 30 $\mu$g to about 600 $\mu$g lovastatin per ml medium, and more preferably from about 250 $\mu$g to about 350 $\mu$g lovastatin per ml of medium. Microorganisms able to survive exposure to lovastatin are selected and analyzed for beta-carotene production. Preferably, the selected microorganisms are deep yellow to yellow-orange in color.

Another class of selective agents of the present invention are inhibitors of acetyl CoA synthesis, such as acetate analogs, propionate analogs, and butyrate analogs. Suitable acetyl CoA synthesis include, but are not limited to, acetoacetanilide, 2-chloroacetamide, chloroacetate, fluoroacetic acid, and mixtures thereof. A preferred acetate analog is acetoacetanilide. In one embodiment of the present invention, mutated spores are plated onto an acetoacetanilide-containing solidified growth medium, such as acetoacetanilide-containing CM17-1, and grown for about 7 days at about 27° C. Preferred concentrations of acetoacetanilide in the medium are from about 400 $\mu$g to about 800 $\mu$g of acetoacetanilide per ml of medium, and more preferably from about 550 $\mu$g to about 650 $\mu$g of acetoacetanilide per ml of medium. Microorganisms that are able to survive exposure to acetoacetanilide are selected and analyzed for beta-carotene production. Preferably, the selected microorganisms are deep yellow to yellow-orange in color.

In another embodiment, a desired mutated microorganism is selected from among all mutated microorganisms by its ability to grow in a medium containing inhibitors of the isoprenoid biosynthetic pathway. Isoprenoid pathway inhibitors are compounds that inhibit one or more steps in the isoprenoid synthetic pathway, including steps in the sterol synthetic pathway. Such inhibitors include, but are not limited to: polyene antibiotics, such as nystatin and amphotericin B; antimycin; citrinin; mevinolin; saponin; phosphorylated farnesyl compounds; azasqualenes; allylamine derivatives; thiocarbamates; pyrimidines; imidazoles; triazoles; morpholines; and mixtures thereof. Preferred isoprenoid inhibitors for use in the present invention are nystatin and amphotericin B, which apparently disrupt cellular membranes by binding to membrane-bound ergosterol and other lipids.

In one embodiment, mutated spores are plated on a nystatin-containing solidified growth medium, such as nystatin-containing CM17-1, and grown for about 7 days at about 27° C. Preferred concentrations of nystatin in the medium are from about 0.1 $\mu$g to about 10 $\mu$g nystatin per ml of medium, more preferably from about 0.5 $\mu$g to about 1.0 $\mu$g nystatin per ml of medium, and even more preferably from about 0.7 $\mu$g to about 0.8 $\mu$g nystatin per ml of medium. Microorganisms able to survive exposure to nystatin are selected and analyzed for beta-carotene production. Preferably, the selected microorganisms are deep yellow to yellow-orange in color.

In another embodiment, mutated spores are plated on an amphotericin B-containing solidified growth medium, such as amphotericin B-containing CM17-1, and grown for about 7 days at about 27° C. Preferred concentrations of amphotericin B in the medium are from about 0.1 $\mu$g to about 10 $\mu$g amphotericin B per ml of medium, and more preferably from about 0.5 $\mu$g to about 1.0 $\mu$g amphotericin B per ml of medium. Microorganisms that are able to survive exposure to amphotericin B are selected and analyzed for beta-carotene production. Preferably, the selected microorganisms are deep yellow to yellow-orange in color.

In yet another embodiment of the present invention, a desired mutated microorganism is selected from among all mutated microorganisms by its ability to grow in a medium containing a compound that inhibits the carotenoid biosynthetic pathway. Inhibitors of the carotenoid biosynthetic pathway are compounds that inhibit one or more steps in the pathway by which carotenoids are synthesized. Carotenoid biosynthesis inhibitors include, but are not limited to: diphenylamine; nicotinic acid; beta-ionone; herbicides, such as norflurazon, metflurazon, phenylfuranones, phenoxynicotinamides, oxyfluorfen, and fluorfen; and mixtures thereof. A preferred carotenoid biosynthesis inhibitor for use in the present invention is beta-ionone. In one embodiment, mutated spores are plated onto beta-ionone-containing solidified growth medium, such as beta-ionone-containing CM17-1, and grown for about 7 days at about 27° C. Preferred concentrations of beta-ionone in the medium are at least about 0.05% beta-ionone. Microorganisms that are able to survive exposure to beta-ionone are selected and analyzed for beta-carotene production. Preferably, the selected microorganisms are deep yellow to yellow-orange in color.

A desired mutated microorganism can also be selected from among all mutated microorganisms by its ability to grow in a medium containing a compound that generates free radicals (i.e., a free radical generator). It is believed that carotenoids, due to their antioxidant properties, are able to protect cells from damage caused by free radicals. However, the present inventors are unaware of the use of free radical generating compounds to select for microorganisms capable of overproducing beta-carotene. Free radical generators include, but are not limited to, quinones, peroxides, UV light, UV-activated photosynthesizers, X-rays, gamma rays, ozone, and mixtures thereof. Preferred free radical generators, such as quinones and peroxides, are those that are easily absorbed by the microorganisms and apparently are not mutagenic. Of these free radical generators, a preferred free radical generator for use in the present invention is duroquinone. In one embodiment, mutated spores are grown on a solidified growth medium, such as CM17-1, containing from about 1 micromolar ($\mu$M) to about 1 millimolar (mM) duroquinone for about 7 days at about 27° C. Microorganisms able to survive exposure to duroquinone are selected and analyzed for beta-carotene production. Preferably, the selected microorganisms are deep yellow to yellow-orange in color.

In accordance with the present invention, the steps of mutation and selection as described above can be carried out one or more times to produce negative and/or positive microorganisms having desired characteristics. A preferred embodiment of the present invention is the use of a pooled mutation and selection technique to produce desired microorganisms. According to this technique, the spores of two or more, preferably from about three to about five, negative microorganisms which have already undergone at least one round of mutagenesis and selection are pooled. The pooled spores are exposed to a mutagen, such as NTG, UV light, and/or EMS, and subsequently exposed to a selective agent from the group described above by plating the spores in a manner such that single colonies form on a solidified growth medium containing the selective agent. Microorganisms able to survive exposure to the selective agent are selected and analyzed for beta-carotene production. Preferably, the selected microorganisms are deep yellow to yellow-orange in color. In a similar manner, positive microorganisms can be pooled, mutated, selected, and analyzed for beta-carotene production.

In accordance with the mutation/selection strategies of the present invention, a negative Mucorales fungal microorganism, preferably of the genus Blakeslea, and more preferably of the species *Blakeslea trispora*, is produced which, when mixed together with a positive Mucorales fungal microorganism, forms a mated culture capable of producing at least about 2.7 grams of beta-carotene per liter medium in about 7 days, preferably at least about 3.5 grams of beta-carotene per liter medium in about 7 days, more preferably at least about 4 grams of beta-carotene per liter medium in about 7 days, even more preferably at least about 6 grams of beta-carotene per liter medium in about 7 days, and even more preferably at least about 7 grams of beta-carotene per liter of medium in about 7 days.

Similarly, the mutation/selection strategies of the present invention lead to the production of a positive Mucorales fungal microorganism, preferably of the genus Blakeslea, and more preferably of the species *Blakeslea trispora*, which, when mixed together with a negative Mucorales fungal microorganism of the present invention, forms a mated culture capable of producing at least about 2.7 grams of beta-carotene per liter medium in about 7 days, preferably at least about 3.5 grams of beta-carotene per liter medium in about 7 days, more preferably at least about 4 grams of beta-carotene per liter medium in about 7 days, even more preferably at least about 6 grams of beta-carotene per liter medium in about 7 days, and even more preferably at least about 7 grams of beta-carotene per liter of medium in about 7 days.

Preferred negative and positive microorganisms of the present invention can be mixed together to form a mated culture capable of producing at least about 65 mg, more preferably at least about 100 mg, even more preferably at least about 175 mg, and even more preferably at least about 200 mg, of beta-carotene per gram dry cell weight.

The amounts of beta-carotene that mated cultures of the present invention are capable of producing can be determined using the procedures outlined in Example 3.

Preferred negative microorganisms of the present invention comprise negative microorganisms of the genus Blakeslea and mutants thereof, wherein such negative microorganisms or mutants thereof, when mated to positive microorganisms of the present invention, form mated cultures which are capable of producing at least about 2.7 grams of beta-carotene per liter in about 7 days.

Similarly, preferred positive microorganisms of the present invention comprise positive microorganisms of the genus Blakeslea and mutants thereof, wherein such positive microorganisms or mutants thereof, when mated to negative microorganisms of the present invention, form mated cultures which are capable of producing at least about 2.7 grams of beta-carotene per liter in about 7 days.

One preferred negative fungal microorganism of the present invention is *Blakeslea trispora* ATCC No. 74147 (PF17-13) which can be characterized by its ability to mate with a positive *B. trispora* microorganism of the present invention to form a mated culture capable of producing at least about 7 grams of beta-carotene per liter of medium in about 7 days. *B. trispora* ATCC No. 74147 (PF17-13) can also be identified by its ability to mate with a positive *B. trispora* microorganism to form a mated culture capable of producing at least about 175 mg, and preferably at least about 200 mg, of beta-carotene per gram dry cell weight. A preferred positive microorganism to mate to *B. trispora* ATCC No. 74147 (PF17-13) is *B. trispora* ATCC No. 74145 (PF17-10).

Another preferred negative fungal microorganism of the present invention is Blakeslea trispora ATCC No. 74146 (PF17-12) which can be characterized by its ability to mate with a positive *B. trispora* microorganism of the present invention to form a mated culture capable of producing at least about 5 grams of beta-carotene per liter of medium in about 7 days. *B. trispora* ATCC No. 74146 (PF17-12) can also be identified by its ability to mate with a positive *B. trispora* microorganism to form a mated culture capable of producing at least about 125 mg beta-carotene per gram dry cell weight. A preferred positive microorganism to mate to *B. trispora* ATCC No. 74146 (PF17-12) is *B. trispora* ATCC No. 74145 (PF17-10).

One preferred positive fungal microorganism of the present invention is *Blakeslea trispora* ATCC No. 74145 (PF17-10) which can be characterized by its ability to mate with a negative *B. trispora* microorganism of the present invention to form a mated culture capable of producing at least about 5 grams of beta-carotene per liter of medium in about 7 days. *B. trispora* ATCC No. 74145 (PF17-10) can also be identified by its ability to mate with a negative *B. trispora* microorganism to form a mated culture capable of producing at least about 125 mg beta-carotene per gram dry cell weight. Preferred negative microorganisms to mate to *B. trispora* ATCC No. 74145 (PF17-10) are *B. trispora* ATCC No. 74147 (PF17-13) and *B. trispora* ATCC No. 74146 (PF17-12).

*Blakeslea trispora* PF17-10, *Blakeslea trispora* PF17-12, and *Blakeslea trispora* PF17-13 were deposited with the American Type Culture Collection, ATCC), 12301 Parklawn Drive, Rockville, Md., 20852-1776, on Mar. 25, 1992, and have been designated ATCC No. 74145 (PF17-10), ATCC No. 74146 (PF17-12), and ATCC No. 74147 (PF17-13). All three microorganisms were deposited under the conditions of the Budapest Treaty on the International Recognition of Deposit of Microorganisms for the purpose of Patent Procedure. All restrictions on the availability to the public of the material so deposited will be irrevocably removed upon the granting of a patent. Deposits will be maintained for a time period of 30 years from the date of deposit or 5 years after the last request for the material, whichever is longer.

It is within the scope of the present invention that any mutation/selection and beta-carotene production techniques described herein for *Blakeslea trispora* can be extended to other species of the genus Blakeslea as well as to other microorganisms of the order Mucorales, and particularly to those of the family Choanephoraceae, due to the similarities between microorganisms within the Mucorales order, particularly with respect to the methods by which Mucorales fungal microorganisms produce beta-carotene.

Another aspect of the present invention relates to the culturing of a mated Mucorales fungal microorganism, formed by the mating of negative and positive Mucorales fungal microorganisms of the present invention, to produce beta-carotene and to the recovery of beta-carotene produced thereby.

In order to produce beta-carotene, negative and positive microorganisms of the present invention are first be cultured in separate fermentation containers in the presence of a vegetative fermentation medium effective to promote mycelial growth. When the negative and positive microorganisms have grown to a desired cell density, they are mixed together at an effective mating ratio to form mated cultures. The mated cultures are then cultured in a production fermentation medium effective to promote beta-carotene production.

It is within the scope of the present invention that the vegetative and production fermentation media share at least some components. Effective vegetative and production fermentation media are generally aqueous solutions which include assimilable sources of carbon, nitrogen, phosphorus, sulfur, magnesium, and other micronutrients.

Sources of assimilable carbon include, but are not limited to: sugars and their polymers, including starches, dextrin, saccharose, maltose, lactose, glucose, mannose, sorbose, arabinose, xylose, levulose, cellobiose, and molasses; fatty acids; and polyalcohols, such as glycerine. Preferred carbon sources include monosaccharides, disaccharides, and trisaccharides. A more preferred carbon source is glucose.

Sources of assimilable nitrogen include, but are not limited to: inorganic nitrogen compounds, such as ammonium salts; and substances of animal, vegetable and/or microbial origin, such as animal fats, plant oils, protein hydrolysates, microbial biomass hydrolysates, soy meal, fish meal, meat meal, meat extract, peptone, tryptone, corn steep liquor, yeast extract, and amino acids.

Vegetative and production fermentation media can also contain other compounds such as vitamins, growth promoters, antioxidants, surfactants, and/or pigment formation promoters, as appropriate.

In one embodiment of the present invention, positive and negative microorganisms are first cultured separately in a vegetative fermentation medium effective to promote growth of the respective microorganisms as mycelia and to prepare the microorganisms for maximum productivity in a production fermentation medium. A preferred vegetative fermentation medium for this purpose is VM17-3, which is an aqueous medium comprising corn flour, potassium phosphate, corn steep liquor, junlon (polyacrylic acid), and thiamine. The fermentation is typically conducted at a temperature from about 26° C. to about 28° C., preferably at about 27° C., and at a pH from about pH 3.7 to about pH 3.9, preferably at about pH 3.8. The vegetative fermentation is conducted until each microorganism culture grows to a desired density, preferably in the range of from about 8 to about 10 grams dry cell weight per liter. Such a cell density can be typically achieved in about 48 hours.

A portion of the positive microorganism-containing culture and a portion of the negative microorganism-containing culture are then both introduced into a production fermentation medium at a ratio to promote effective mating. As used herein, a production fermentation medium is a medium that is effective both in promoting the mating of positive and negative microorganisms to form a mated culture and in promoting the production of beta-carotene.

One aspect of the present invention is the importance of the balance, or ratio, between the amount of negative and positive microorganisms added to the production fermentation medium to initiate mating. As used herein, the "mating ratio" is the approximate number of negative microorganisms added per positive microorganism. As used herein, the approximate number of microorganisms corresponds to the volume of microorganisms added multiplied by the cell density in the volume (i.e., [ml of culture added]×[cells/ml culture]). Since negative and positive microorganisms are typically grown to the same cell density, the ratio of volumes added to the production fermentation medium approximately corresponds to the ratio of number of microorganisms added.

An "effective mating ratio" is a ratio of negative microorganisms per positive microorganisms which leads to the formation of a mated culture capable of overproducing beta-carotene. Researchers have typically mixed negative and positive microorganisms together at a mating ratio of about one negative microorganism per positive microorganism. However, a 1:1 mating ratio requires that the separate vegetative fermentations of the negative and positive microorganisms be precisely controlled to yield equal numbers of both negative and positive microorganisms. It would be more desirable to carry out beta-carotene production fermentations in which only a small percentage of positive microorganism was required per negative microorganism, thereby allowing one to carry out smaller vegetative fermentations of positive microorganisms. It is preferred to use more negative microorganisms and fewer positive microorganisms because, while not being bound by theory, it is believed that negative microorganisms are better producers of beta-carotene. However, negative microorganisms apparently must either be mated to positive microorganisms or administered beta-factor in order to produce significant amounts of beta-carotene.

According to the present invention, the amount of positive microorganisms required per amount of negative microorganism can be dramatically reduced without interfering with beta-carotene production. The use of mating ratios of, for example, about 2, 4, 10, 20, 40, 80, and 200 negative microorganisms per positive microorganism does not decrease beta-carotene production. In one embodiment of the present invention, the mating ratio is at least about 2 negative microorganisms per positive microorganism and can be as high as at least about 200 negative microorganisms per positive microorganism, preferably from about 200 to about 1000 negative microorganisms per positive microorganism. Preferably the mating ratio is at least about 4 negative microorganisms per positive microorganism, and more preferably at least about 10 negative microorganisms per positive microorganism, and even more preferably at least about 40 negative microorganisms per positive microorganism. Even more preferably, the mating ratio is from about 40 to about 200 negative microorganisms per positive microorganism.

One production fermentation medium of the present invention, denoted FM17-A, is an aqueous medium comprising Pharmamedia (a cottonseed-derived protein material purchased from Traders Oil Mill Co., Fort Worth, Tex.), glucose, potassium phosphate, manganese sulfate, soybean oil, cottonseed oil, dextrin, Triton X-100, ascorbic acid, lactic acid, thiamine, and isoniazid. A preferred medium is FM17-B in which isoniazid is replaced by kerosene, which appears to stimulate beta-carotene production at least as well as isoniazid. About 48 to about 54 hours after adding the negative and positive microorganisms to the production fermentation medium, an antioxidant (preferably ethoxyquin) and a beta-carotene inducer (preferably beta-ionone) are added to the medium. Other suitable beta-carotene inducers include, but are not limited to: citrus derivatives, including citrus pulps and citrus oils, such as limonene; and TCA cycle precursors and intermediates, such as alpha-ketoglutarate. The production fermentation is preferably conducted at a pH of from about pH 6.2 to about pH 6.7, more preferably at about pH 6.5, and at a temperature of from about 26° C. to about 28° C., more preferably at about 27° C.

Another production fermentation medium of the present invention, denoted NM-1, is an aqueous medium comprising cottonseed oil, soybean flour, potassium phosphate, manganese sulfate, and thiamine. About 48 hours to about 54 hours after mating, beta-carotene production is induced by the addition of, for example, beta-ionone. Other beta-carotene inducers can be used as a substitute for, or in addition to, beta-ionone, including, but not limited to: kerosene; isoniazid; citrus derivatives, including citrus pulps and citrus oils, such as limonene; and TCA cycle precursors and intermediates, such as alpha-ketoglutarate. The production fermentation is preferably conducted at a pH of from about pH 6.2 to about pH 6.7, more preferably at about pH 6.5, and at a temperature of from about 26° C. to about 28° C., more preferably at about 27° C.

NM-1 has several advantages including low viscosity, ease of sterilization, and simple composition. Fungi grown in this medium do not clump, despite the low viscosity of the medium.

Beta-carotene production can be accomplished by culturing microorganisms of the present invention in a variety of conventional fermentation modes including, but not limited to, shake flasks, batch fermentors, fed-batch fermentors, and semi-continuous fermentors. It is well known to one skilled in the art that production typically increases when fermentations are carried out in a fermentor as opposed to a shake flask, generally because higher cell densities can be achieved in a fermentor and because the conditions in a fermentor are typically more favorable for faster growth, leading to shorter production times. As such, mated cultures of the present invention that are capable of producing at least about 2.7 grams, preferably at least about 3.5 grams of beta-carotene per liter medium in about 7 days, more preferably at least about 4 grams of beta-carotene per liter medium in about 7 days, even more preferably at least about 6 grams of beta-carotene per liter medium in about 7 days, and even more preferably at least about 7 grams of beta-carotene per liter of medium in about 7 days in shake flasks, are likely capable of producing similar titers in about 4 days in a fermentor.

Beta-carotene production can be measured in several ways, including, but not limited to, spectrophotometric and chromatographic analysis. Spectrophotometry is particularly useful to obtain beta-carotene production levels, such as titers. Reverse phase high performance liquid chromatography is particularly useful both to quantitate beta-carotene production and to distinguish between different beta-carotene species.

Beta-carotene produced in accordance with the present invention can be recovered and used in a variety of ways, including, as an enhancer of pigmentation, as a nutritional (vitamin A) supplement, as an enhancer of lactation, as an enhancer of fertility, as an anticancer agent, as a cardiovascular therapeutic agent, and as an agent to reduce damage caused by reactive oxygen species and phototoxic molecules.

Since beta-carotene is retained within the microorganism after synthesis, beta-carotene can be recovered as a beta-carotene-containing biomass. As used herein, a beta-carotene-containing biomass refers to a composition produced by separating beta-carotene-overproducing microorganisms from a fermentation medium and treating such microorganisms as necessary to make the beta-carotene bioavailable. Suitable separation techniques include, but are not limited to, centrifugation and filtration. As used herein, separation refers to the removal of a substantial amount of medium from the microorganisms.

Suitable treatments include those that result in cell lysis, such as physical, chemical, or enzymatic methods. Treating "as necessary" can range from no treatment to a treatment resulting in complete cell lysis. One of the advantages of Blakeslea is that microorganisms of this genus apparently do not require treatment to make beta-carotene bioavailable, at least for some species to which beta-carotene may be administered. That is, humans and other animals that consume beta-carotene-containing Blakeslea microorganisms are likely to be able to digest Blakeslea cell walls in order to obtain beta-carotene.

In one embodiment, beta-carotene-containing fungal microorganisms are separated from the fermentation medium by rotovap filtration to remove a substantial portion of the liquid, washed with an aqueous solvent, and spray dried to form a substantially dry beta-carotene-containing biomass powder. Preferably the powder contains at least about 10% (wt/wt) beta-carotene, more preferably at least about 17.5% (wt/wt) beta-carotene, and even more preferably at least about 20% (wt/wt) beta-carotene.

Alternatively, beta-carotene can be recovered free from the microorganisms that produced it as a beta-carotene-containing formulation. In one embodiment, beta-carotene-containing Blakeslea are separated from the fermentation medium and lysed. Suitable separation techniques include, but are not limited to, centrifugation and filtration. Lysis can be accomplished using, for example, physical, chemical, or enzymatic methods. Beta-carotene can be extracted from the lysed fungi using an extracting agent and condensed using molecular distillation. Suitable extracting agents include, but are not limited to, supercritical fluids and oil-based solvents, such as sunflower oil, vegetable oils, castor oil and light mineral oil. The recovered beta-carotene-containing formulation is preferably at least about 5% beta-carotene in oil, and more preferably from about 20% to about 30% beta-carotene in oil.

Beta-carotene produced in accordance with the present invention can be used as a feed additive to enhance the pigmentation of animal foodstuffs. As used herein, animal foodstuffs are animals which are raised as food, such as, but not limited to, poultry, fish and crustaceans. Beta-carotene can also be used to enhance the pigmentation of substances such as foods and cosmetics. As used herein, enhancement of pigmentation describes a method by which administration of an effective amount of beta-carotene to a foodstuff or addition of an effective amount of beta-carotene to a substance imparts a yellow to yellow-orange color to the substance (e.g., food products and cosmetics) or to the flesh, skin, other body parts, and/or egg yolks of the animal foodstuff.

Beta-carotene produced according to the present invention can be used as a Vitamin A supplement in animals, such as humans, which are capable of converting beta-carotene into Vitamin A. As used herein, an effective amount of beta-carotene to serve as a Vitamin A supplement, is an amount of beta-carotene which when ingested by an animal and converted into Vitamin A provides sufficient Vitamin A to be an effective Vitamin A supplement.

Beta-carotene can also be administered to animals, such as bovine animals, to increase lactation and fertility in an amount effective to increase lactation or fertility.

In another embodiment of the present invention, beta-carotene produced according to the present invention can be used to prevent or treat cancer or cardiovascular disease or to reduce damage caused by reactive oxygen species and phototoxic molecules. As used herein, reactive oxygen species are molecules that oxidize other molecules, often leading to, or resulting in, cell or tissue damage. Reactive oxygen species include photosensitizers, singlet oxygen, and oxygen free radicals. As used herein, phototoxic molecules refer to agents, such as light, which can degrade or otherwise inactivate light-sensitive compounds, and which can cause tissue damage (including cell and organ damage) in plants and animals. An effective amount of beta-carotene is an amount which effectively prevents or reduces damage caused by reactive oxygen species and/or phototoxic molecules.

For example, beta-carotene may be used in mammals, preferably humans, to prevent or treat certain forms of cancer or to reduce both external and internal cellular, tissue or organ damage caused by reactive oxygen species, particularly to the cardiovascular system. For example, beta-carotene may be used to lower the incidence of heart attacks. While not being bound by theory, it is believed that the anti-oxidizing activity of beta-carotene can block low density lipoproteins from being deposited as plaque in arteries. Furthermore, beta-carotene may be used to block free radical damage that often occurs after heart attacks.

Beta-carotene-containing biomasses and formulations can be administered either internally (including, but not limited to, oral administration) or externally (including, but not limited to, topical administration). For example, a beta-carotene-containing formulation can be added to sunscreens and other oils and lotions to reduce damage to the skin caused by reactive oxygen species.

Beta-carotene-containing formulations can also be contacted with (e.g, added to) light-sensitive and/or oxygen-sensitive compounds, including foods, in an effective amount to stabilize and reduce damage caused to such compounds in the presence of light or oxygen.

The following experimental results are provided for purposes of illustration and are not intended to limit the scope of the invention.

EXAMPLE 1

This Example describes the use of mutation and selection strategies of the present invention to produce several negative *Blakeslea trispora* microorganisms, including *B. trispora* ATCC No. 74146 (PF17-12) and *B. trispora* ATCC No. 74147 (PF17-13).

Negative microorganism *Blakeslea trispora* ATCC No. 14272 was subjected to multiple rounds of mutation and selection, leading to the production of negative microorganisms 13-29, 13-36, 13-75, 13-109, and 13-113, as shown in Table 1. Spore suspensions of these five negative microorganisms were pooled and submitted to mutagenesis using NTG (N-methyl-N'-nitro-N-nitrosoguanidine), as shown in Table 2a.

TABLE 1

Genealogy of Negative Microorganisms

```
           ATCC 14272
             | NTG
            14-38
             | NTG
           28-163
              |
    ┌─────────┴─────────┐
   | EU                 | Re
   4-76                 16-9
    | NTG               | NTG
   15-73                29-104
    | Re
   21-9
```

TABLE 1-continued
Genealogy of Negative Microorganisms

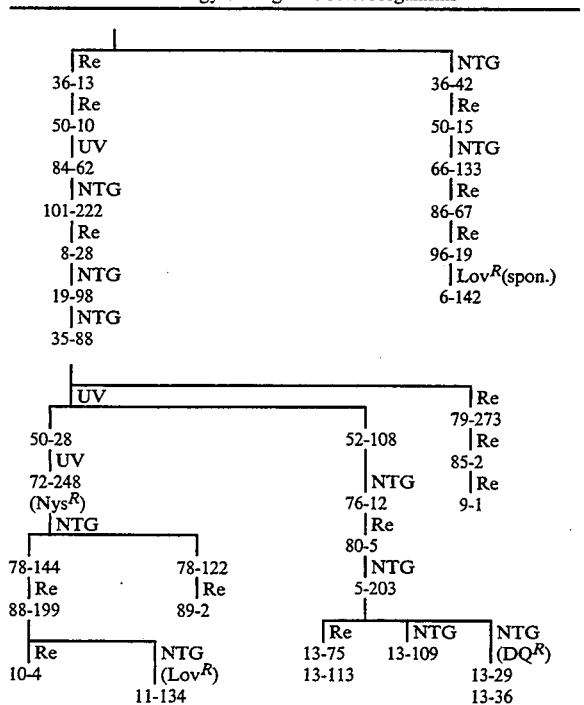

Nys$^R$: nystatin resistant mutant
Lov$^R$: lovastatin resistant mutant
DQ$^R$: duroquinone resistant mutant
EU: UV and ethylmethane sulfonate
NTG: N-methyl-N'-nitro-nitrosoguanidine
Re: reisolate of parental strain

TABLE 2
Pooling of Negative Microorganisms

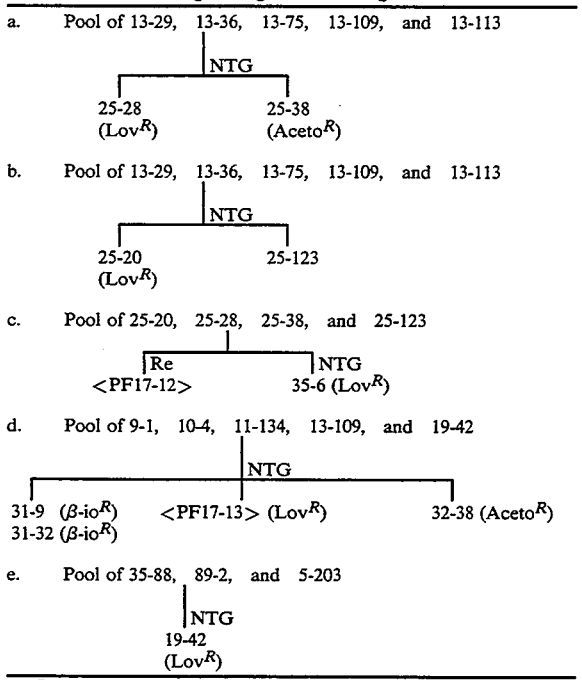

Lov$^R$: lovastatin resistant mutant
Aceto$^R$: acetoacetanilide resistant mutant
β-io$^R$: β-ionone resistant mutant
Re: reisolate of parental strain Spore suspensions were obtained by thawing vials of frozen spores preserved in a solution of 10% glycerol and 5% lactose. For each microorganism, about 0.1 ml of spores were pipetted onto a PDA slant. APDA slant contains, per liter of water, 39 grams of Difco", potato dextrose agar, 2 mg of thiamine·HCl, and 5 g of Bacto"-agar, at a final pH of about pH 5.9. The spore-containing PDA slants were incubated at about 27° C. for at least about 7 days. Five ml of sterile water was then added to the slant to suspend the spores. The concentration of spores in the suspension was about $3 \times 10^5$ spores per ml.

A suspension containing about 50,000 spores of negative B. trispora microorganisms 13-29, 13-36, 13-75, 13-109, and 13-113 was centrifuged and the spores resuspended in 5 ml of 50 mM Tris(hydroxymethyl)aminomethane (Tris) buffer at a pH of about 8.0. NTG was added to a final concentration of about 50 μg NTG per ml of buffer, and the spores were incubated for about 20 to 25 minutes at room temperature. (These conditions typically kill 30% to 60% of the cells.) The mutated spores were washed in 100 mM phosphate buffer at about pH 7.0, prior to spreading onto CM17-1 solidified growth media plates that also contained either about 300 μg lovastatin per ml of medium or about 600 μg acetoacetanilide per ml of medium in order to identify negative microorganisms which when mated to positive microorganisms form mated cultures capable of overproducing beta-carotene. CM17-1 contains, per liter of water, 3 grams of glucose, 200 mg of L-asparagine, 50 mg of MgSO$_4$·7H$_2$O, 150 mg of KH$_2$PO$_4$, 25 μg thiamine·HCl, 100 mg of yeast extract, 100 mg of sodium deoxycholate, and 20 grams of agar. The pH of CM17-1 is about pH 5.3 to about pH 5.5. The lovastatin-containing or acetoacetanilide-containing CM17-1 plates were incubated at about 27° C. for about 6 to about 8 days and colonies having a color indicative of beta-carotene production were isolated.

A deep yellow negative microorganism, denoted B. trispora 25-28, was isolated from the lovastatin-containing plate. Mating of B. trispora 25-28 to a positive microorganism, such as B. trispora ATCC No. 74145 (PF17-10) led to a mated culture which produced at least about 4.5 grams of beta-carotene per liter in about 7 days when cultured in a shake flask as described in Example 3.

A yellow-orange negative microorganism, denoted B. trispora 25-38, was isolated from the acetoacetanilide-containing plate. Mating of B. trispora 25-38 to a positive microorganism, such as B. trispora ATCC No. 74145 (PF17-10) led to a mated culture which produced at least about 4 grams of beta-carotene per liter in about 7 days when cultured in a shake flask as described in Example 3.

In a second pooling experiment using spore suspensions of B. trispora negative microorganisms 13-29, 13-36, 13-75, 13-109, and 13-113 (see Table 2b), the pooled spores were exposed to NTG as described above, plated on CM17-1 solidified growth medium either with or without about 300 μg lovastatin per ml of medium, and incubated for about 6 to about 8 days at about 27° C. One negative microorganism, denoted B. trispora 25-20, was isolated from a plate containing lovastatin. A second negative microorganism, denoted B. trispora 25-123, was isolated from a plate without lovastatin.

Spore suspensions of B. trispora negative microorganisms 25-28 and 25-38 were mixed with spore suspensions of B. trispora negative microorganisms 25-20 and 25–123, as shown in Table 2c. The pooled mixture was exposed to NTG as described above, spread onto CM17-1 plates, and incubated for about 6 to about 8 days at about 27° C. to isolate colonies with pigmentation indicative of beta-carotene production. A dark yellow negative microorganism, denoted *B. trispora* ATCC No. 74146 (PF17-12) was isolated. Mating of *B. trispora* ATCC No. (PF17-12) to a positive microorganism, such as *B. trispora* ATCC No. 74145 (PF17-10) led to a mated culture which produced at least about 5 grams of beta-carotene per liter in about 7 days, and at least about 125 mg of beta-carotene per gram dry cell weight, when cultured in a shake flask as described in Example 3.

In another pooled mutation/selection experiment, a pooled spore suspension of *B. trispora* negative microorganisms 9-1, 10-4, 11-134, 13-109, and 19-42 were exposed to NTG as described above (see Table 2d; also see Tables 1 and 2e for the genealogies of 9-1, 10-4, 11-134, 13-109, and 19-42). Mutated spores were spread onto CM17-1 plates containing either 0.1% beta-ionone, 300 μg lovastatin per ml, or 600 μg acetoacetanilide per ml, and incubated at about 27° C. for about 6 to about 8 days to identify negative microorganisms which when mated to positive microorganisms form mated cultures capable of overproducing beta-carotene. Two yellow negative microorganisms, denoted *B. trispora* 31-9 and 31-22, were isolated from beta-ionone-containing CM17-1 medium. A dark yellow negative microorganism, denoted *B. trispora* 32-38, was isolated from acetoacetanilide-containing CM17-1 medium. A yellow-orange negative microorganism, denoted *B. trispora* ATCC No. 74147 (PF17-13), was isolated from lovastatin-containing CM17-1 medium.

Mating of *B. trispora* ATCC No. 74147 (PF17-13) to a positive microorganism, such as *B. trispora* ATCC No. 74145 (PF17-10) led to a mated culture which produced at least about 7 grams of beta-carotene per liter in about 7 days, and at least about 175 mg, and preferably at least about 200 mg, of beta-carotene per gram dry cell weight, when cultured in a shake flask as described in Example 3.

EXAMPLE 2

This Example describes the use of mutation and selection strategies of the present invention to produce positive *Blakeslea trispora* microorganism ATCC No. 74145 (PF17-10).

A spore suspension of the positive microorganism *Blakeslea trispora* ATCC 14271 was mutated by exposure to UV light, spread onto CM17-1 plates, and incubated at about 27° C. for about 6 to about 8 days to identify a positive microorganism which when mated to a negative microorganism forms a mated culture capable of overproducing beta-carotene. A bright yellow positive microorganism, denoted *B. trispora* ATCC No. 74145 (PF17-10), was isolated. Mating of *B. trispora* ATCC No. 74145 (PF17-10) to a negative microorganism, such as *B. trispora* ATCC No. 74147 (PF17-13) led to a mated culture which produced at least about 7 grams of beta-carotene per liter in about 7 days, and at least about 175 mg of beta-carotene per gram dry cell weight, when cultured in a shake flask as described in Example 3.

EXAMPLE 3

This Example demonstrates the influence of mating ratios on the ability of mated cultures to produce beta-carotene.

A two-stage fermentation was carried out to produce beta-carotene. In the first stage, separate vegetative fermentations were carried out for negative and positive *B. trispora* microorganisms. One 250–300 ml non-baffled shake flask containing about 30 ml of VM17-3 vegetative fermentation medium was inoculated with about 0.5 ml of a spore suspension (about $2 \times 10^4$ spores) of negative microorganism *B. trispora* ATCC No. 74147 (PF17-13). A second 250–300 ml non-baffled shake flask containing about 30 ml of VM17-3 vegetative medium was inoculated with the same amount of a spore suspension of positive microorganism *B. trispora* ATCC No. 74145 (PF17-10). VM17-3 medium contains, per liter water, 35 grams of corn flour, 500 mg of $KH_2PO_4$, 2.5 grams of corn steep powder, 2 grams of junlon (polyacrylic acid), and 2 mg of thiamine·HCl, at a pH of about pH 3.7 to about pH 3.9. The negative and positive microorganisms were each cultured in a New Brunswick Scientific G-53 shaker at about 250 rpm for about 48 hours at about 27° C. in a high humidity environment (about 60% to about 80% humidity), and achieved a cell density of from about 8 to about 10 grams dry cell weight per liter of medium.

In the second (production) stage, about 2 ml of the vegetatively grown *B. trispora* ATCC No. 74147 (PF17-13) culture was removed from the VM17-3 medium and added to about 30 ml of FM17-A production fermentation medium in a 250–300 ml non-baffled shake flask, along with about 0.05 ml, 0.1 ml, 0.2 ml, or 0.5 ml, respectively, of the positive microorganism *B. trispora* ATCC No. 74145 (PF17-10), to give mating ratios of about 40, 20, 10, and 4 negative microorganisms, respectively, per positive microorganism. FM17-A medium contains, per liter water, 75 grams of Pharmamedia, 10 grams of glucose, 100 mg of $MnSO·H_2$, O, 500 mg of $KH_2PO_4$, 30 grams (w/v) of soybean oil, 30 grams (w/v) of cottonseed oil, 60 grams of dextrin, 1.2 grams (w/v) of Triton X-100, 6 grams (w/v) of ascorbic acid, 2 grams (w/v) of lactic acid, 2 mg of thiamine·HCl, and 0.075% isoniazid. The medium is adjusted to a pH of about pH 6.5 with 50% sodium hydroxide.

The mated cultures were incubated at about 27° C. at about 250 rpm in a New Brunswick Scientific G-53 shaker. About 54 hours after culturing was initiated in FM17 medium, beta-ionone (0.1%) and ethoxyquin (0.025%) were added to the medium. The fermentation was continued for an additional 5 days.

Beta-carotene production was measured using the following procedure. About 8 ml of the mated culture is homogenized for about 20 seconds at 75% maximum speed with a Brinkmann" homogenizer in a 15 ml polycarbonate tube. About 0.1 ml of the homogenate is transferred into a previously tared $16 \times 125$ mm screw cap test tube containing about 10 4-mm glass beads. The weight of the homogenate is recorded to at least three significant figures and typically is about 0.100 grams $\pm 0.05$ grams. The homogenate is vortexed for about 5 minutes on a multi-tube vortexer set at about 90% maximum speed. About four ml of ethanol are added and vortexing is continued for an additional 20 seconds. About four ml of hexane containing 1 mg/ml butylated hydroxytoluene (hexane/BHT) is then added and the sample vortexed for an additional 5 minutes. About one ml of water is then added, followed by mild hand mixing. The tube is then centrifuged at 2,000 rpm for about 2 minutes in order to separate the beta-carotene-containing hexane phase. A sample of the hexane phase is diluted with hexane, typically at a dilution factor of about 100-fold. The absorbance of the sample at about 450 nm is then determined, and the beta-carotene concentration calculated. The extinction coefficient for beta-carotene is determined experimentally by dissolving a known weight of pure carotenoid in hexane, and measuring the absorbance at about 450 nm. Under these conditions, the extinction coefficient is about 2620. Typically, beta-carotene production values are confirmed by reverse phase high performance liquid chromatography (HPLC) analysis.

A comparison of the amount of beta-carotene produced using different mating ratios is depicted in Table 3. Table 4 shows the results of a similar experiment in which the negative microorganism B. trispora ATCC No. 74146 (PF17-12) was used in place of B. trispora ATCC No. 74147 (PF17-13). Both sets of tabulated data indicate that negative : positive mating ratios of about 40:1 lead to at least as much, if not more, beta-carotene production as do mating ratios of about 4:1.

TABLE 3

Influence of Mating Ratios on Beta-Carotene Production for Mated Cultures Formed from PF17-13 and PF17-10

| Mating Ratio PF17-13:PF17-10 | Beta-Carotene Titer (g/l) |
| --- | --- |
| 4:1 | 2.7 |
| 10:1 | 3.7 |
| 20:1 | 4.1 |
| 40:1 | 4.6 |

TABLE 4

Influence of Mating Ratios on Beta-Carotene Production for Mated Cultures Formed from PF17-12 and PF17-10

| Mating Ratio PF17-12:PF17-10 | Beta-Carotene Titer (g/l) |
| --- | --- |
| 4:1 | 3.8 |
| 10:1 | 3.7 |
| 20:1 | 4.0 |
| 40:1 | 4.0 |

EXAMPLE 4

This Example shows that even at mating ratios as high as 200 negative microorganisms per positive microorganism, beta-carotene production remains high. B. trispora ATCC No. 74147 (PF17-13) (denoted "−") and B. trispora ATCC No. 74145 (PF17-10) (denoted "+") were grown and mated as described in Example 3, except that the following mating ratios were used: about 40, 80, and negative microorganisms per positive microorganism. Production fermentations and determination of beta-carotene concentrations were also conducted as in Example 3, except that three shake flask fermentations were conducted for each mating ratio. As shown in Table 5, beta-carotene production was very similar for all three mating ratios.

TABLE 5

Influence of Mating Ratios on Beta-Carotene Production

| Mating Ratio (−/+) | Beta-Carotene Titer (g/l) | Average Titer (g/l) |
| --- | --- | --- |
| 40:1 | 4.8 | 5.4 ± 0.6 |
|  | 5.9 |  |
|  | 5.6 |  |
| 80:1 | 5.0 | 5.4 ± 0.4 |
|  | 5.5 |  |
|  | 5.7 |  |
| 200:1 | 5.6 | 5.6 ± 0.5 |
|  | 6.1 |  |
|  | 5.1 |  |

EXAMPLE 5

This Example compares the effects of kerosene and isoniazid on beta-carotene production Negative microorganism B. trispora ATCC No. 74147 (PF17-13) and positive microorganism B. trispora ATCC No. 74145 (PF17-10) were cultured separately in VM17-3 medium to promote vegetative growth of the microorganisms as described in Example 3. Four shake flask experiments (A through D) were set up to compare the ability of kerosene and isoniazid to stimulate beta-carotene production. For each flask, negative and positive microorganisms were added to about 30 ml of production fermentation medium in a negative:positive mating ratio of about 40:1 as described in Example 3. The production fermentation media was FM17 (FM17-A without isoniazid). About 48 to 54 hours after culturing was initiated in FM17 medium, beta-ionone (0.1%) and ethoxyquin (0.025%) were added to each of the flasks.

The following additions were also made to each flask: Isoniazid (0.075%) was added to Flask A at the beginning of the production fermentation phase. Kerosene (4%) was added to Flask B at about 24 hours after the initiation of the production phase. Kerosene (4%) was added to Flask C at about 51 hours after the initiation of the production phase. Both isoniazid (0.075%) and kerosene (4%) were added to Flask D, isoniazid addition being at the initiation of the production phase, and kerosene addition being at about 51 hours after the initiation of the production phase. Except for these variations, the production fermentations were carried out as described in Example 3, and the results are shown in Table 6.

TABLE 6

Use of Kerosene to Promote Beta-Carotene Production

| Expt. | Production Medium | Beta-Carotene Titer (g/l) |
| --- | --- | --- |
| A | FM17 + 0.075% isoniazid at 0 hr | 4.45 |
| B | FM17 + 4% kerosene at 24 hr | 4.10 |
| C | FM17 + 4% kerosene at 51 hr | 4.70 |
| D | FM17 + 0.075% isoniazid at 0 hr + 4% kerosene at 51 hr | 4.20 |

A second set of experiments was conducted to compare different amounts of kerosene. Otherwise, the fermentations were conducted as described above. The results are shown in Table 7.

TABLE 7

Effect of Different Concentrations of Kerosene

| Expt. | Production Medium | Beta-Carotene Titer (g/l) |
| --- | --- | --- |
| E | FM17 + 4% kerosene at 51 hr | 4.90 |
| F | FM17 + 2% kerosene at 51 hr | 5.80 |
| G | FM17 + 1% kerosene at 51 hr | 5.00 |

These results show that kerosene stimulates similar if not better beta-carotene titers compared to isoniazid.

While various embodiments of the present invention have been described in detail, it is apparent that modifications and adaptations of those embodiments will occur to those skilled in the art. It is expressly understood, however, that such modifications and adaptations are within the scope of the present invention, as set forth in the following claims:

What is claimed is:

1. A positive *Blakeslea trispora* microorganism having all of the identifying characteristics of *Blakeslea trispora* ATCC No. 74145 (PF17-10), or mutants of the microorganism which, when mated in an effective mating ratio to a negative *Blakeslea trispora* microorganism, forms a mated culture capable of producing at least about 3.5 grams of beta-carotene per liter in about 7 days.

2. The positive microorganism of claim 1, wherein the negative *Blakeslea trispora* microorganism has all of the identifying characteristics of deposited strain ATCC No. 74146 (PF17-12) or deposited strain ATCC No. 74147 (PF17-13).

3. The positive microorganism of claim 2, wherein the negative *Blakeslea trispora* microorganism is deposited strain ATCC No. 74146 (PF17-12).

4. The positive microorganism of claim 2, wherein the negative *Blakeslea trispora* microorganism is deposited strain ATCC No. 74147 (PF17-13).

5. A mated *Blakeslea trispora* culture capable of producing at least about 3.5 grams of beta carotene per liter of production fermentation medium in about 7 days, wherein the mated culture comprises an effective mating ratio of a negative *Blakeslea trispora* microorganism having all of the identifying characteristics of deposited strains ATCC No. 74146 (PF17-12) or ATCC No. 74147 (PF17-13) and a positive *Blakeslea trispora* microorganism having all of the identifying characteristics of deposited strain ATCC No. 74145 (PF17-10).

6. The mated culture of claim 5 wherein the negative *Blakeslea trispora* microorganism is deposited strain ATCC No. 74146 (PF17-12).

7. The mated culture of claim 5 wherein the negative *Blakeslea trispora* microorganism is deposited strain ATCC No. 74147 (PF17-13).

8. The mated culture of claim 5 wherein the positive *Blakeslea trispora* microorganism is deposited strain ATCC No. 74145 (PF17-10).

9. The mated culture of claim 5 capable of producing at least about 4 grams of beta-carotene per liter of medium in about 7 days.

10. The mated culture of claim 5 capable of producing at least about 7 grams of beta-carotene per liter of medium in about 7 days.

11. The mated culture of claim 5 capable of producing at least about 65 mg of beta-carotene per gram dry cell weight.

12. The mated culture of claim 5 capable of producing at least about 175 mg of beta-carotene per gram dry cell weight.

13. The mated culture of claim 5, wherein the mating ratio comprises at least about 10 negative microorganisms per positive microorganism.

14. The mated culture of claim 5, wherein the mating ratio comprises at least about 40 negative microorganisms per positive microorganism.

15. The mated culture of claim 5, wherein the mating ratio comprises from about 40 to about 200 negative microorganisms per positive microorganism.

16. The mated culture of claim 5 which is formed by a method comprising:
 (a) culturing the negative *Blakeslea trispora* microorganism and the positive *Blakeslea trispora* microorganism, separately in vegetative fermentation media effective to promote growth of the microorganisms; and
 (b) mixing together an effective mating ratio of the negative *Blakeslea trispora* microorganisms and the positive *Blakeslea trispora* microorganisms.

17. A method for producing beta-carotene comprising culturing the mated *Blakeslea trispora* culture of claim 16.

18. The method of claim 17, wherein the mating ratio comprises at least about 10 negative microorganisms per positive microorganism.

19. The method of claim 17, wherein the mating ratio comprises at least about 40 negative microorganisms per positive microorganism.

20. The method of claim 17, wherein the mating ratio comprises from about 40 to about 200 negative microorganisms per positive microorganism.

21. A beta-carotene-containing biomass produced by a method comprising:
 (a) culturing in an effective production fermentation medium a mated *Blakeslea trispora* culture capable of producing at least about 3.5 grams of beta carotene per liter of production fermentation medium in about 7 days, wherein the mated culture comprises an effective mating ratio of a negative *Blakeslea trispora* microorganism having all of the identifying characteristics of deposited strains ATCC No. 74146 (PF17-12) or ATCC No. 74147 (PF17-13) and a positive *Blakeslea trispora* microorganism having all of the identifying characteristics of deposited strain ATCC No. 74145 (PF17-10); and
 (b) separating the mated culture from the medium to form a beta-carotene-containing biomass.

22. The biomass of claim 21 wherein the negative *Blakeslea trispora* microorganism is deposited strain ATCC No. (PF17-12).

23. The biomass of claim 21 wherein the negative *Blakeslea trispora* microorganism is deposited strain ATCC No. (PF17-13).

24. The biomass of claim 21 wherein the positive *Blakeslea trispora* microorganism is deposited strain ATCC No. (PF17-10).

25. The biomass of claim 21 comprising at least about 10% (wt/wt) beta-carotene.

* * * * *